(12) United States Patent
Landegren et al.

(10) Patent No.: US 7,306,904 B2
(45) Date of Patent: *Dec. 11, 2007

(54) METHODS AND KITS FOR PROXIMITY PROBING

(75) Inventors: Ulf Landegren, Uppsala (SE); Simon Fredriksson, Uppsala (SE)

(73) Assignee: Olink AB, Uppsala (SE)

( * ) Notice: Subject to any disclaimer, the term of this patent is extended or adjusted under 35 U.S.C. 154(b) by 1122 days.

This patent is subject to a terminal disclaimer.

(21) Appl. No.: 09/785,657

(22) Filed: Feb. 20, 2001

(65) Prior Publication Data

US 2002/0064779 A1 May 30, 2002

Related U.S. Application Data

(60) Provisional application No. 60/183,371, filed on Feb. 18, 2000.

(51) Int. Cl.
*C12Q 1/68* (2006.01)
*C07H 21/04* (2006.01)
*C07K 14/00* (2006.01)

(52) U.S. Cl. .................. 435/6; 536/24.31; 536/24.32; 530/350

(58) Field of Classification Search .............. 435/6, 435/7.2; 536/23.1, 24.31, 24.32; 530/300, 530/350
See application file for complete search history.

(56) References Cited

U.S. PATENT DOCUMENTS 4,988,617 A * 1/1991 Landegren et al. ............ 435/6
5,871,921 A * 2/1999 Landegren et al. ............ 435/6
6,306,587 B1 * 10/2001 Royer et al. .................. 435/6
6,511,809 B2 * 1/2003 Baez et al. .................... 435/6

FOREIGN PATENT DOCUMENTS

| EP | 0 320 308 A2 | | 6/1989 |
| WO | WO 93/06240 A1 | | 4/1993 |
| WO | WO 97/00446 | * | 1/1997 |
| WO | WO 97/00446 A1 | | 1/1997 |
| WO | WO 9700446 A1 | * | 1/1997 |
| WO | WO 9732044 A1 | * | 9/1997 |

OTHER PUBLICATIONS

Hart, Hiram and Elaine Greenwald, "Scintillation Proximity Assay (SPA)- A New Method of Immunoassay", Molecular Immunology, vol. 16, pp. 265-267, 1979.
Szöllösi, János, et al., "Application Of Fluorescence Resonance Energy Transfer In The Clinical Laboratory: Routine And Research", Cytometry (Communications in Clinical Cytometry), vol. 34, pp. 159-178, 1998.
Li, Fusheng, et al., "Homogeneous Noncompetitive Immunoassay Based on the Energy Transfer Between Fluorolabeled Antibody Variable Domains (Open Sandwich Fluoroimmunoassay)", BIOTECHNIQUES, VOL. 27, No. 4, pp. 738-743, 1999.
Koo, Edward, et al., "Amyloid Diseases: Abnormal Protein Aggregation In Neurodegeneration", Proc. Natl. Acad. Sci., vol. 96(18), pp. 9989-9990, Aug. 1999.
Prusiner, Stanley, et al. "Scrapie Prions Aggregate To Form Amyloid-Like Birefringent Rods", CELL, vol. 35 (2 Pt 1), pp. 349-358, Dec. 1983.
Nadeau, James, et al. "Real-Time, Swequence-Specific Detection of Nucleic Acids During Strand Displacement Amplification", Analytical Biochemistry, vol. 276, pp. 177-187, 1999.
van Deursen, Peter, et al., "A Novel Quantitative Multiplex NASBA Method: Application to Measuring Tissue Factor and CD14 mRNA Levels in Human Monocytes", Nucleic Acids Research, vol. 27, No. 17, pp. I-vi, 1999.
White, Stephanie, and Theodore Christopoulos, "Signal Amplification System for DNA Hybridization Assays Based on In Vitro Expression of a DNA Label Encoding Apoaequorin", Nucleic Acids Research, vol. 27, No. 19, pp. i-viii, 1999.
Kwiatkowski, Robert, et al., "Clinical, Genetic, and Pharmacogenetic Applications of Invader Assay", Molecular Diagnosis, vol. 4, No. 4, pp. 353-364, 1999.
Gibson, Ursula, et al. "A Novel Method for Real Time Quantitative RT-PCR", Genome Research, vol. 6, pp. 995-1001, 1996.
Tyagi Sanjay and Fred Russell Kramer, "Molecular Beacons: Probes that Fluoresce upon Hybridization", Nature Biotechnology, vol. 14, pp. 303-308, Mar. 1996.
Steuerwald, Nury, et al., "Analysis of Gene Expression in Single Oocyte and Embryos by Real-Time Rapid Cycle Fluorescence Monitored RT-PCR", Molecular Human Reproduction, vol. 5, No. 11, pp. 1034-1039, 1999.
Gentalen, Erik and Mark Chee, "A Novel Method for Determining Linkage Between DNA Sequences: Hybridization to Paired Probe Arrays", Nucleic Acids Research, vol. 27, No. 6, pp. 1485-1491, 1999.
Banér, Johan, et al. "Signal Amplification of Padlock Probes by Rolling Circle Replication", Nucleic Acids Research, vol. 26, No. 22, pp. 5073-5078, 1998.
Nilsson, Mats, et al., "Padlock Probes: Circularizing Oligonucleotides for Localized DNA Detection", SCIENCE, vol. 265, pp. 2085-2088, Sep. 30, 1994.
Gold, Larry, et al., "Diversity of Oligonucleotide Functions", Annu. Rev. Biochem., vol. 64, pp. 761-797, 1995.
Green, Louis, et al., "Inhibitory DNA Ligands to Platelet-Derived Growth Factor B-Chain", BIOCHEMISTRY, vol. 35, pp. 14413-14424, 1996.

* cited by examiner

*Primary Examiner*—Suryaprabha Chunduru
(74) *Attorney, Agent, or Firm*—Browdy and Neimark, PLLC

(57) ABSTRACT

The present invention relates to sensitive, rapid and convenient assays for detection and/or quantification of one or several analyte(s) in solution using so called proximity probes. The proximity probes comprise a binding moiety and a nucleic acid. The nucleic acid from one proximity probe is only capable of interaction with the nucleic acid from the other proximity probe when these are in close proximity, i.e. have bound to the analytes for which they are specific. The present invention relates to methods and kits for proximity probing and are performed in solution without the need of a solid phase.

21 Claims, 6 Drawing Sheets

Figure 10:
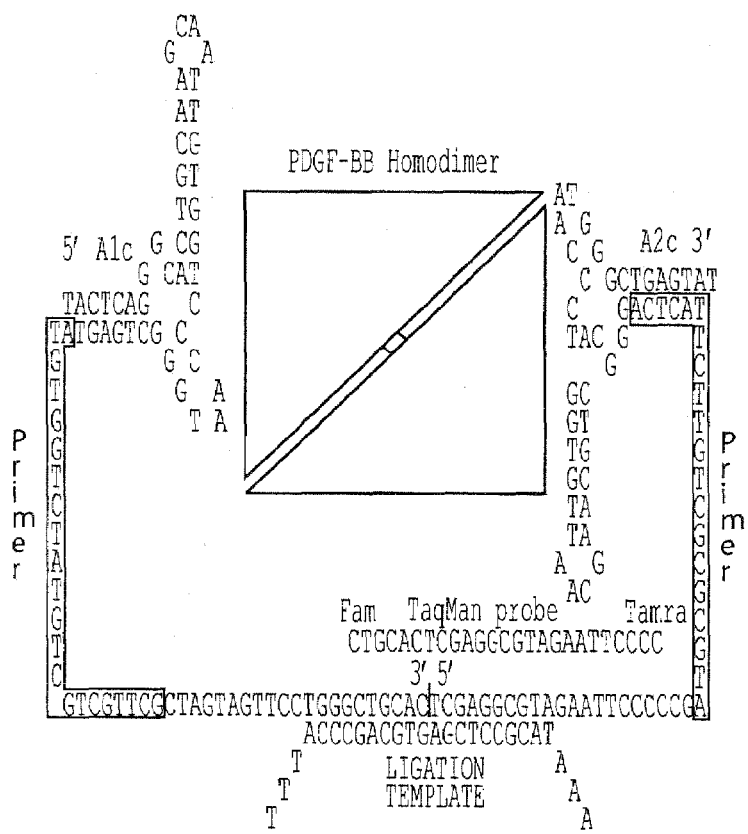

Figure 1. Definition of symbols
 Binding moiety
 Analyte
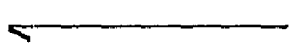 Oligonucleotide, 3' end shown with arrow
 Proximity probe, oligonucleotide with free 5' end
 Proximity probe, oligonucleotide with free 3' end
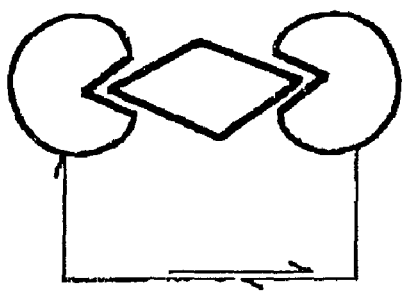 Ligation of proximity-probes bound to target analyte Figure 2. Template promoted ligation variants

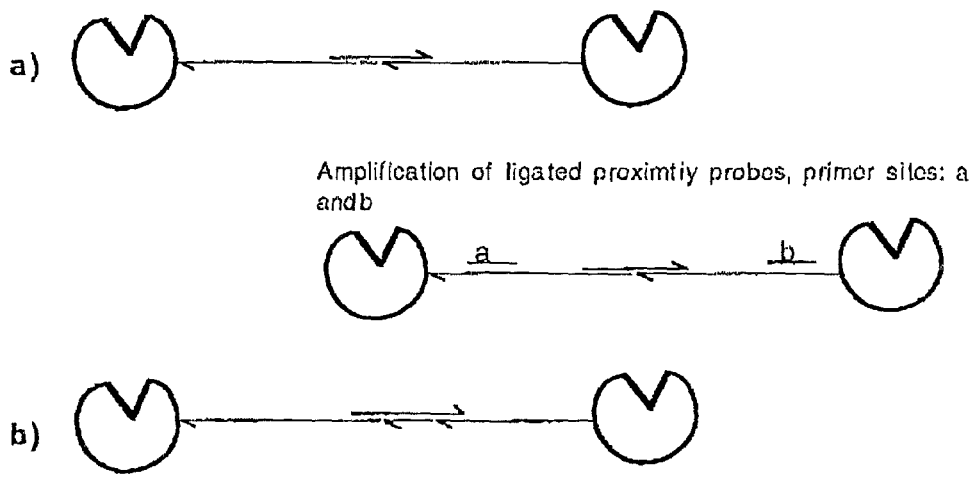

Figure 3. Fill-in polymerisation prior to ligation

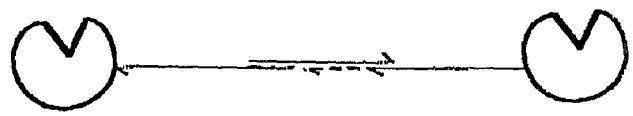

Figure 4. Ligation of supplementary oligonucleotides, x and y, to the proximity-probe-hybridisation oligonucleotide z. Amplification primer sites a and b.

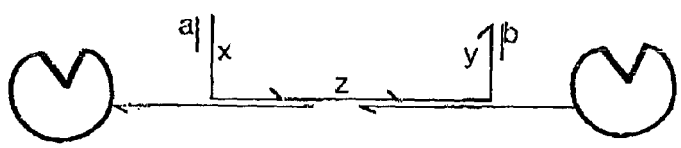

Figure 5. Generation of circular DNA, for rolling circle amplification

Figure 6. Priming of rolling circle amplification by a proximal oligonucleotide

Figure 7. Template unassisted ligation by T4 RNA ligase
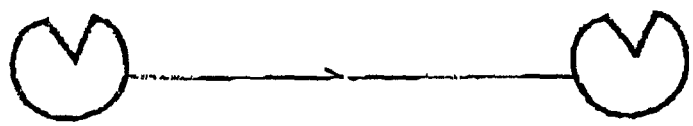
Figure 8. Both probes with free 3'- ends capable of hybridising to each other.
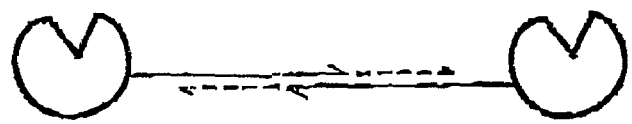
Figure 9. Requirement of two ligation events, using three binding moieties. Amplification primer sites a and b.
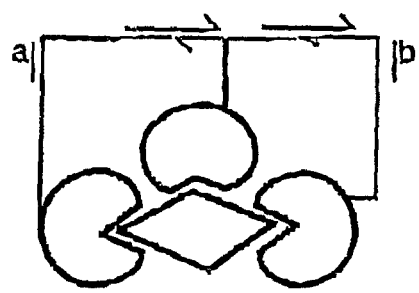

METHODS AND KITS FOR PROXIMITY PROBING

The present application claims the benefit of U.S. Provisional Appln. No. 60/183,371, filed Feb. 18, 2000.

FIELD OF THE INVENTION

The present invention is within the medical field. More precisely, the invention relates to sensitive, rapid and convenient assays for detection and/or quantification of one or several analytes in solution using so called proximity probes.

BACKGROUND OF THE INVENTION

Most protein detection assays rely on the efficient separation of target bound detector reagents from non-bound reagents. The assay sensitivity is crucially dependent on this separation and the power of the reporter system used. For the separation, a solid phase is usually employed containing an immobilised affinity reagent for the analyte with a secondary affinity reagent for the detection, as in a sandwich ELISA. In the operation of washing off unbound detector reagents the stringency must be carefully balanced. At high stringency of washing the background is lower at the cost of reduced detection signal of analytes and at low stringency the probability of detection is higher, but at the cost of higher background.

Assays that use a solid phase require considerable time and effort for the analysis. The binding of reagents and analytes to the surface is a time consuming process and the washing steps must be precisely and reproducibly controlled between samples to give exact results. Solid phase assays are also more difficult to automate than homogenous assays.

Assays that do not require a solid phase and the associated washing steps have important advantages. Such homogenous assays exist, for example the scintillation proximity assay (1) and assays based on fluorescence resonance energy transfer (2, 3). However these suffer from a low sensitivity due to poor signal to noise ratios.

In WO 97/00446 an ultrasensitive immunoassay and kit is described using two reagents that are crosslinked if they adhere to an analyte. The coincident binding of two analytes give rise to an interaction product, which may be selected so that it can serve as a template in amplification reactions, increasing specificity through the requirement for dual recognition and reducing the risk for non-specific signals. This immunoassay is performed on a solid support.

SUMMARY OF THE INVENTION

This invention is characterised by its ability to detect and quantify one or several analytes in solution in a homogenous one tube assay with high sensitivity and specificity. So called, proximity-probes comprising a binding moiety with affinity for the analyte and also a reactive functionality, are added to the sample solution. These probes are then permitted to interact with one another and will do so to a greater extent if two or more proximity-probes have bound the same individual analyte molecule. Since the proximity-probes are capable of binding the analyte at multiple sites, the analyte acts in a way analogous to a catalyst by bringing the reactive probes closer to one another and increasing their ability to interact through an increased local concentration. The interaction between the coupled functionalities results in a detectable signal in a secondary reaction.

In the standard procedure for the method, the analytes may be proteins, nucleic acids or any other molecule of interest capable of specifically binding two or more proximity-probes. One or more analyte(s) may be detected/quantified. Also aggregations of one analyte into a multimeric complex consisting of one protein or peptide type may be detected/quantified as well as complexes of two or more different molecules close to each other.

Complexes of different proteins can also be detected by the assay. In such a case, the proximity-probes bind to two different proteins, but gain proximity if these two proteins are close to each other.

Several neurological disorders are caused by the formation of protein aggregates, so called amyloidal plaques. Alzheimer's disease, Parkinson's disease, Creutzfeldt-Jakob's disease, motor neuron disease, and Huntington's disease, arc some examples (4). As these diseases progress, more and more aggregates form. If these aggregates could be detected at an early stage of the disease, proper medical attention could be given to the patient. Detecting the existence of prion proteins, which cause scrapie, is another example of aggregate forming proteins (5). These aggregates are ideal analytical targets for proximity-probing. Since an aggregate contains many copies of the same protein, a proximity-probe specific for this protein would bind at multiple sites along the aggregate. These proximity-probes will thereby gain proximity upon binding the aggregate. The high sensitivity of proximity-probing could detect such aggregate formation at an early disease stage. The invention also relates to detection/quantification of protein aggregates comprising proteins of different types, such as antibodies and antigens. The existence of infectious prion protein aggregates in food is also of great importance, This is expected to be of great importance for detection/quantification according to the invention of infectious agents causing BSE (bovine spongiform encephalitis) and the human counter part CJD (Creutzfeldt-Jacobs disease).

The binding moieties of the proximity-probes may be proteins such as monoclonal and polyclonal antibodies, peptides, lectins, nucleic acids, carbohydrates, soluble cell surface receptors, combinatorially derived protein from phage display or ribosome display or any other type of binding moiety. Combinations of binding moieties may also be used.

The reactive functionality of a proximity-probe is comprised of a nucleic acid coupled to the binding moiety. This coupling may be a covalent crosslinking or non-covalent, as can be exemplified in a streptavidin-biotin coupling. As proximity-probes are brought near each other, for example when pair wise bound to the target analyte, the coupled nucleic acids are also brought in vicinity of each other. The proximity of these target bound nucleic acids is used to promote various detectable interactions between these nucleic acids. This nucleic acid interaction is detected in a secondary step of the analysis. In most cases the secondary detection of the amount of nucleic acid interaction will involve a specific amplification of the interaction product.

In the case of two proximity probes, one of the binding moieties will typically have a certain nucleic acid sequence coupled to it by its 5' end while the other binding moiety has a nucleic acid sequence coupled to it by its 3' end. The 5' proximity-probe thus has a free 3' hydroxyl capable of reacting with the 5' phosphate of the second binding moiety through interaction.

The reactive functionalities (nucleic acids) present on these binding moieties are capable of pair wise reacting when present at a high concentration. In the detection procedure the proximity-probes are added to a sample at a low concentration. The concentration of the proximity-probe is set so low that the proximity-probes will not react with each other to any great extent when the proximity-probes are not near each other. But when two or more the proximity-probes bind to the analyte the high local concentration promotes interaction between the probes, resulting in a detection signal exceeding the analyte independent background signal.

The product of the ligation reaction will in most cases exist at a very low concentration in need of an amplification step in order to detect it. The resulting ligation between these nucleic acids is readily amplifiable by several reactions, such as polymerase chain reaction (PCR), strand displacement amplification (6), NASBA (7), RNA transcription (8), invader assay (9). These amplification reactions are thus designed only to give a product when the two nucleic acids have been crosslinked by ligation. This is done by placing the primers for PCR or SDA, one on each conjugated nucleic acid. The amplification reaction can be followed in real-time by sequence specific TaqMan probes (10) or molecular beacons probes (11) or by using non-sequence specific intercalating fluorescent dyes such as SYBR green (12), The resulting product can also be quantified by electrophoresis in gels.

In some cases, a lot of ligation product is produced. It can then be directly analysed without the need of an amplification. Several methods can then be employed. For example, the first of the two united nucleic acid sequences can be designed to contain a sequence capable of binding through hybridisation to an immobilised oligonucleotide probe. Upon binding the oligonucleotide probe, the second nucleic acid sequence will also bind since the two are now linked by the ligation. All non bound sequences can be washed of and a labelled hybridisation probe specific for the second sequence will bind and detect the ligation product.

The two united nucleic acids may be analysed in a hybridisation based assay where the united sequence elements bind cooperatively and thereby much stronger than non united ones to an oligonucleotide probe. Such probes may be constructed in DNA microarrays to selectively bind nucleic acids with united sequence elements (13).

Thus, in a first aspect the invention relates to a method for detecting and/or qualifying one or more analyte(s) in solution, characterised by
  a) binding of two or more proximity probes to a respective binding site on said analyte(s), wherein the proximity probes are comprised of a binding moiety and a thereto coupled (conjugated or via linkage, such as a biotin-streptavidin linkage) nucleic acid, also sometimes referred to as a reactive functionality;
  b) allowing the binding moiety to bind to the analyte(s) and allowing the nucleic acids to interact with each other if they are in close proximity to each other; and
  c) detection and/or quantification of the degree of interacton between the nucleic acids with the proviso that binding moieties and the analyte(s) not all comprise nucleic acid.

In a second aspect, the invention relates to a kit for detecting and quantifying one or more analyte(s) in solution, comprising
  a pair of proximity probes comprising binding moieties with affinity for the analyte(s) and each provided with a nucleic acid (reactive functionality) capable of interacting with each other. In a preferred embodiment, one nucleic acid has a free 3' end and the other has a free 5' end.

The following components can optionally be added in the kit:
  a ligase and a splint template for joining the nucleic acids; and
  primers which hybridise to each of the nucleic acids.

In further aspects, the invention relates to use of the method and/or the kit according the invention for the following purposes:
  for screening for ligand-receptor interaction antagonists a high throughput screening procedure;
  for competitive detection and/or quantifying of an unknown analyte in solution;
  for screening ligand candidates in a large pool;
  for screening of drug candidates from large libraries;
  for detection of infectious agents.

In a further aspect, the invention relates to a method for screening for ligand-receptor interaction antagonists, characterised by
  reacting two proximity probes having
  a) a binding moiety with affinity for the receptor ligand and
  b) a thereto bound (conjugated or via linkage, such as a biotin-streptavidin linkage) nucleic acid with the receptor-ligand and its receptor and samples of potential ligand receptor interaction antagonists in a high throughput screening procedure; wherein a positive signal is generated when an antagonist is present.

Another aspect of the invention relates to a method for detecting and quantifying an unknown analyte in solution, characterised by
  reacting a proximity probe comprising
  a) a binding moiety with affinity for the analyte and
  b) a thereto bound nucleic acid with an analyte with thereto bound nucleic acid in the solution containing the unknown analyte;
  allowing the analyte with thereto bound nucleic acid to compete with the unknown analyte for binding to the binding moiety;
  allowing the nucleic acids to bind to each other; and
  detection and quantification of the amount of binding events between the nucleic acids, wherein the signal from the reaction is inversely proportional to the concentration of the unknown analyte.

Yet a further aspect of the invention relates to a method for detecting and quantifying an unknown analyte in solution, characterised by
  reacting a receptor coupled to a nucleic acid (reactive functionality) with its receptor-ligand coupled to a nucleic acid (reactive functionality);
  allowing the nucleic acids to interact with each other;
  detection and/or quantification of the degree of interaction between the nucleic acids, wherein the detection signal will be decreased if a molecule blocking the receptor ligand complex is present.

Choice of Ligase Enzymes and Templates

The ligation reaction is dependent on a hybridised template strand (also called DNA splint or splint template) when using a DNA ligase enzyme such as T4 DNA ligase. The two oligonucleotides to be ligated must hybridize to the template with the 3' end of one oligonucleotide lined up to the 5' phosphate of the other.

When the ligation template is added to the reaction it may hybridise to a pair of nearby proximity-probes and promote ligation. But if each proximity-probe oligonucleotide has bound a ligation template no ligation will occur since no since ligation template spans pairs of ligatable ends. If the ligation template is added at a high concentration the probability for a one to one hybridisation will be greater. But if the proximity-probes have bound their target, the high local concentration of their oligonucleotides will favour a generation of appropriate ligation substrates. This mechanism serves to promote ligation in the presence of analyte, and to inactivate proximity-probes in the absence of antigens, improving the signal to noise ratio.

The template should be designed so as to not give rise to any false amplification products. If incorrectly designed the ligation template may be used by the amplification enzyme, such as DNA polymerase, as a template for polymerisation. This extension, templated by the ligation template, may give rise to false products. To overcome this problem, DNA oligonucleotides may be ligated with an RNA oligonucleotide as template using the T4 DNA ligase enzyme. Taq DNA polymerase can not use RNA as a template for polymerisation, hence no false PCR products can arise from polymerisation on such a ligation template. A DNA splint with 2 short hybridisation regions (such as 10+10) also works like the RNA splint. But since the hybridisation is weak they will not template polymerisation at the high temperature of the PCR, due to the low melting temperature.

Alternative means to react the conjugated oligonucleotides is through the T4 RNA ligase which does not need any template strand, or to use chemical ligation to join ends that cannot prime polymerisation reactions.

Competitive Dummy Probes

The background signal arising from ligated proximity-probe oligonucleotides which have not bound the target may be decreased by adding a dummy oligonucleotide. This oligonucleotide shall have the ability to ligate to either oligonucleotide conjugated to the target binding moiety through the same ligation template used in the regular ligation. However a ligation between this dummy oligonucleotide and the proximity-probe oligonucleotides will not give rise to any PCR reaction since the dummy oligonucleotide is designed to not contain the primer site required for PCR. The concentration of the dummy oligonucleotide is optimised to where it will readily ligate with the non-target bound proximity-probe oligonucleotides, but not compete in ligation with the target bound proximity-probes due to their high local concentration.

Preincubation, Followed by Dilution and Ligation for Low Affinity Ligands

In the case of detecting a target with proximity-probes of low affinity and slow binding kinetics a preincubation with the proximity-probes at a sufficiently high concentration for most analytes to be bound by probes is preferred. This preincubation is then quickly diluted in a large volume of cold buffer, and a portion of this dilution is subsequently added to a ligation reaction mixture. This ligation reaction mixture contains the template, ATP and ligase enzyme. The ligation mix also contain the detection components as described above. The low temperature will minimise the dissociation of existing proximity-probe-target complexes while the vast dilution, will result in a decrease of the concentration of the proximity-probe oligonucleotides thereby lowering their reactivity and minimising the background signal. The dilution will also to a lesser extent decrease the true positive signal.

Blocking Probes for Complex Samples and Sample Dilution

Samples of a high complexity, such as serum samples, contain many proteins other than the analyte of interest. When using DNA aptamers this causes a problem since they may unspecifically bind to other proteins in the solution besides the analyte. The assay should use as little probe as possible in order not to increase the background, so if the sample is complex the signal from analyte bound probes may decrease and the background increase due to the need to supply more probes. This can be overcome by adding a blocking molecule that will block out unspecific interactions by the analyte specific probes. Such a molecule may be an aptamer which resembles the specific one but does not have any high affinity for the analyte, or the ligatable ends.

Another way to overcome this problem is by diluting the complex sample prior to the analysis. This will greatly decrease the amount of proteins the probes may bind unspecifically to and thereby one can use a lower concentration of probes. The analyte will in this case also be diluted, but the high sensitivity of the proximity probing will still give a good detection and quantification.

DETAILED DESCRIPTION OF THE INVENTION

There are several ways in which the oligonucleotides coupled to the binding moeities may interact when in proximity, FIGS. 1-8 represent some examples. These interaction examples can also be used in combinations. Ligation reactions are not limited to enzymatically catalysed ligation but can be performed by chemical ligation, or catalysed by catalytic RNA or DNA.

FIG. 1 explains the symbols used.

FIG. 2a) represents the hybridisation of a template oligonucleotide for ligation of proximity-probe oligonucleotides. This ligation can be detected via amplification by placing PCR primers, one on each proximity-probe oligonucleotide.

FIG. 2b) Shows an additional oligonucleotide ligated in-between the proximity-probe oligonucleotides.

FIG. 3) Shows a DNA polymerase catalysed "fill-in" reaction primed by a proximity-probe oligonucleotide, followed by ligation of the proximity-probe pair.

FIG. 4) Shows the use of a first hybridisation oligonucleotide (z) which binds to both proximity-probe oligonucleotides. Two other oligonucleotides (x and y) hybridise one to each proximity-probe-oligonucleotide and ligate forming an x-z-y oligonucleotide which is specifically detected. When the proximity-probes are not near each other, one oligonucleotide z will hybridise to all proximity-probe oligonucleotides. This disables the formation of any x-z-y ligation product, only forming x-z and z-y.

FIG. 5) Generation of circular DNA (ligated padlock probe)(15), by ligation of two oligonucleotides, templated by the proximity-probe oligonucleotides. The circular DNA may be amplified by rolling circle amplification(14).

FIG. 6) Ligation of one oligonucleotide, templated by hybridising to one proximty-probe oligonucleotide, resulting in a circle (ligated padlock probe). The circular DNA is readily primed for rolling circle amplification when the second proximity-probe oligonucleotide is proximity of the formed circle. The proximity is provided by target bindings.

FIG. 7) Shows the ligation of two proximity-probe oligonucleotides without the requirement of a hybridised template, T4 RNA ligase can catalyse a non templated ligation, and does so preferentially when the proximity-probe oligonucleotides are near each other.

FIG. 8) Shows priming and templating of DNA polymerisation by the proximity-probes. The two proximity-probe oligonucleotides are weakly hybridised to each other and this hybridisation is stabilised cooperatively by analyte binding. This hybridisation and subsequent polymerisation reaction is optimised to occur preferentially when the proximity-probes are in proximity.

FIG. 9) Shows the ligation of three proximity-probes bound to the same analyte, requiring two ligation events for signal. The proximity-probe oligonucleotides are ligated and primer sites for amplification are placed to span over all three oligonucleotides.

FIG. 10 is a schematic drawing of PDGF-BB bound by two aptamer based proximity-probes, A1c (SEQ ID NO:1) and A2c (SEQ ID NO:2). The aptamer sequence which binds PDGF-BB is shown in close to the protein. The TaqMan probe sequence (reverse complement of SEQ ID NO:3) used in PCR detection is shown. The ligation junction between the proximity-probes is marked with a line between the 3' end of A1c and the 5' end of A2c. The primer sites are boxed. The ligation template is SEQ ID NO:4.

Figure 11:
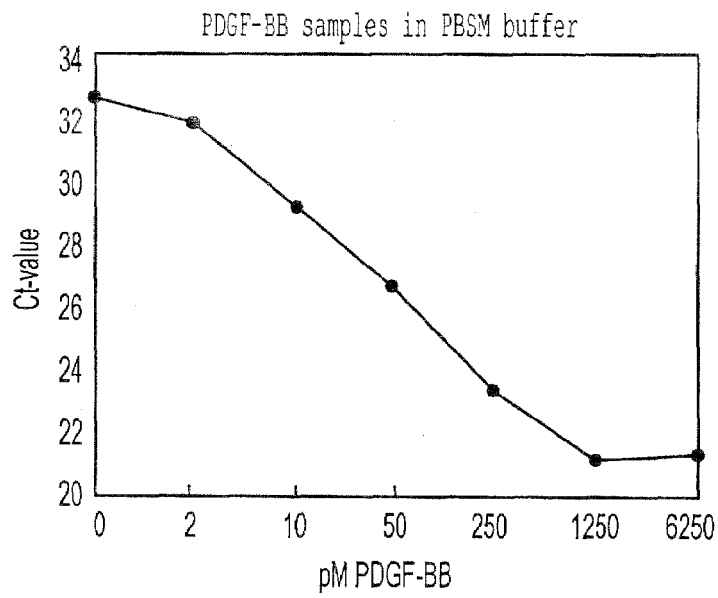

FIG. 11. Results of proximity-probing of PDGF-BB using separate ligation and amplification/detection mixes. 1 uL of sample from a dilution series was analysed. The amount of ligation was quantified by the 5' exonuclease TaqMan PCR assay. A high Ct value corresponds to a low amount of ligation generated PCR templates.

Figure 12:
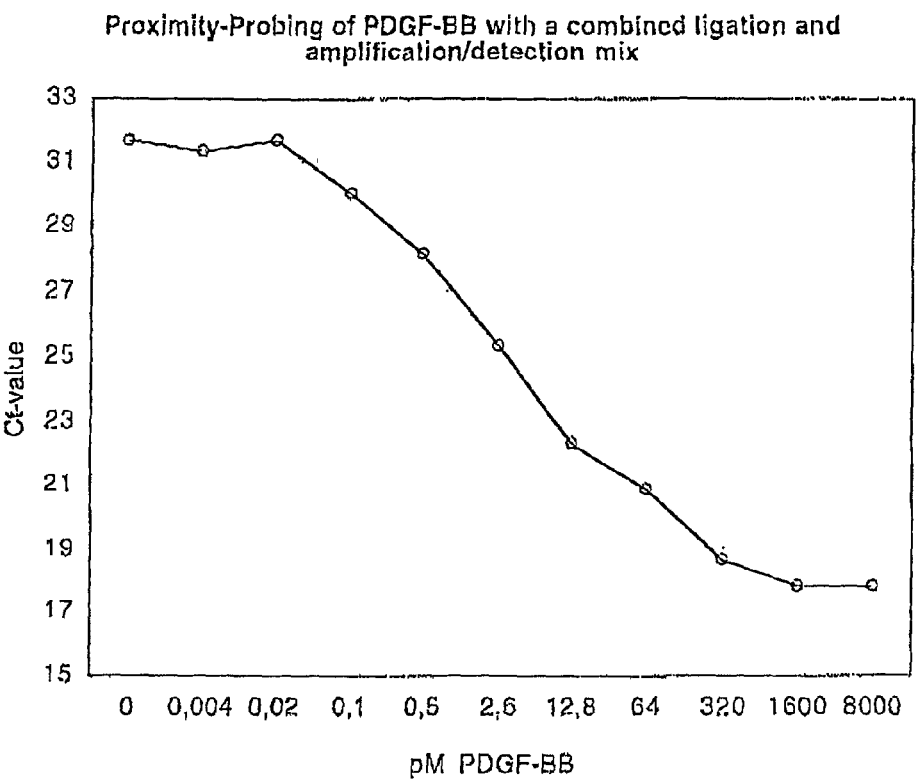

FIG. 12. Results of proximity-probing of PDGF-BB using a combined ligation and amplification mix, 1 uL of sample was analysed. A high Ct-value corresponds to a low amount of ligation generated PCR templates.

Figure 13:
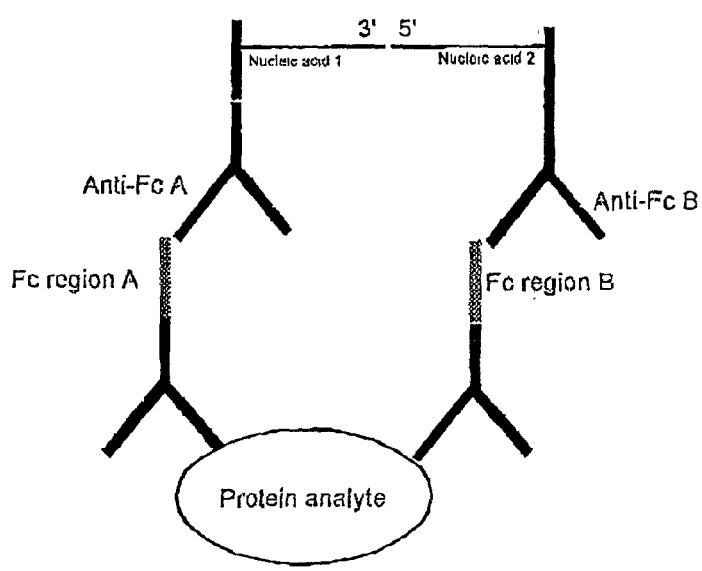

FIG. 13. Example of universal proximity-probes, based on antibodies capable of binding to several primary antibody types.

Figure 14:
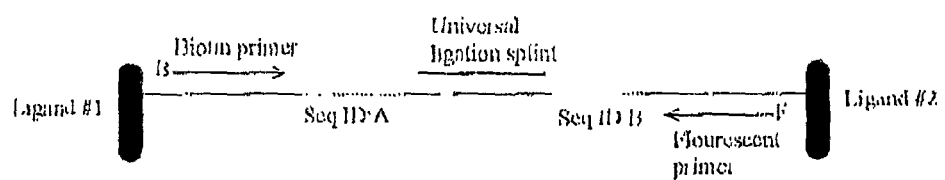

FIG. 14. Example of a proximity-probe pair used in a multiplex analysis. A positive signal is generated when the two matching sequence identification tags (ID:A and ID:B) are united. Two PCR primers are shown, one containing a biotin residue for making the product single stranded prior to DNA microarray hybridisation, and the other with a fluorescence marker for detection.

EXAMPLE 1

PDGF Detection using SELEX Derived Aptamers

An example of proximity probing is an assay capable of the detecting platelet derived growth factor BB (PDGF BB). In this case the binding moieties which bind the protein at two sites are Selex (Systematic evolution of ligands by exponential enrichment)-derived aptamers (16). These are single stranded oligonucleotides selected repeatedly from very large random combinatorial libraries for affinity towards a target protein, in this case the B-chain of PDGF (17). The aptamer sequences are easily extended to contain additional polynucleotide sequence besides the binding moiety. This extension contains the reactive functionality mentioned above. One aptamer has a 5' extension ending in a 5' phosphate group and the other aptamer has a 3' extension ending in a 3' hydroxyl. These two extensions may be united through a ligation reaction if they are hybridised to a template strand (FIG. 10).

The efficiency of such a ligation reaction is dependent on the concentration of the two proximity-probes. If these are in low concentration the reaction efficiency may be greatly increased by the presence of a molecule (analyte) capable of binding the two proximity-probes together, thus increasing their local concentration and promoting the reaction between the reactive functionalities or extensions. PDGF acts as such a "catalyst" by bringing together two aptamers with 3' or 5' extensions respectively. If the proximity-probes are added at a concentration of 5 pM the increase in effective concentration is estimated at 15 million times when the proximity-probes have bound PDGF.

The amount of PDGF present in the sample is proportional to the threshold cycle value (Ct-value) of the TaqMan assay, used in the course of a PCR reaction. Since PDGF BB is a homodimer the same binding moiety (selex aptamer) can be used for both proximity-probes. Statistically, half of the two probe/one PDGF complexes will be of the 3'-probe/PDGF/5'-probe type, while the 3'-probe/PDGF/3'-probe and 5'-probe/PDGF/5'-probe complexes will not result in any detectable signal.

Experimental Procedure for Proximity-probing of PDGF BB

To analyse several samples, three stock mixes of reagents are prepared. The first mix is the incubation mix with which the unknown sample is incubated for 1 to 2 hours at room temperature. This mix includes the two proximity-probes (selex aptamer and ligatable sequence). After the incubation, the ligation mix is added for five minutes at room temperature. This mix contains the ligase enzyme, a ligation template, and ATP. The ligation reaction is inactivated by heating the reaction to 80 degrees for 20 minutes. Finally, the amplification/detection mix contains PCR primers, TaqMan probe, dNTPs and DNA polymerase. The PCR amplification is detected in real-time with the TaqMan assay and the Ct-value reflects the amount of PDGF present in the sample. The ct-value is the threshold cycle where the PCR reaction reaches a critical amount of amplification product has been generated. FIG. 11 shows the Ct-values for a dilution of PDGF-BB in a PBSM buffer. A high ct-value corresponds to a low, or undetectable PDGF-BB concentration.

Incubation mix: volume 14 µL, 50 mM KCl, 10 mM Tris-HCl pH 8.3, BSA 0,01%, 3 mM MgCl2, 7.5 pM probe A1c and A2c. 1 µL of sample is added to this mix.

Ligation mix: volume 5 µL, 50 mM KCl, 10 mM Tris-HCl pH 8,3, 3 mM MgCl2, 0.8 mM ATP, 20 nM ligation template, 3 Weiss units T4 DNA ligase.

Amplification detection mix (TaqMan PCR): volume 30 µL, 50 mM KCl, 10 mM Tris-HCl pH 8.3, 0.4 mM MgCl2, 0.33 mM dNTPs, 1x buffer A, 1 µM forward primer, 1 µM reverse primer, 83 nM TaqMan probe, 1.56 Units AmpliTaq Gold polymerase (Perkin-Elmer).

Probe A1c: (SEQ ID NO:1)

TACTCAGGGCACTGCAAGCAATTGTGGTCCCAATGGGCTGAGTATGTGGTCTATGTCGTC

GTTCGCTAGTAGTTCCTGGGCTGCAC

Probe A2c (SEQ ID NO:2)

TCGAGGCGTAGAATTCCCCCGATGCGCGCTGTTCTTACTCAGGGCACTGCAAGCAATTG

TGGTCCCAATGGGCTGAGTAT

-continued

Splint template for ligation (6+20):  (SEQ ID NO:3)

GGGGGAATTCTACGCCTCGAGTGCAG

Frw primer:  (nucleotides 44-65 of SEQ ID NO:1)

ATGTGGTCTATGTCGTCGTTCG

Rew primer:  (reverse complement of nucleotides 22-41 of SEQ ID NO:2)

TGAGTAAGAACAGCGCGCAT

Taq Man probe A1+2c:  (reverse complement of SEQ ID NO:3)

Fluor-CTGCACTCGAGGCGTAGAATTCCCC-Tamra

PCR cycles: hold 10 min 95, cycle 95 (15 sec)-60 (1 min) 45 times

Combined Ligation Mix and Per Mix for Higher Sensitivity

The two mixes for ligation and per detection may be combined and added in one step. The incubation mix remains the same, with sample and reactive probes. The incubation is preferably done in a small volume and upon addition of the ligation/detection mix the volume is significantly increased, thus diluting the unbound proximity-probes and decreasing their reactivity. However, the analyte-bound proximity-probes maintain their high local concentration aid high reactivity since a new equilibrium does not have time to set during the short ligation reaction.

FIG. 12 shows the result of such a combined ligation/detection variant of proximity probing with selex aptamers detecting PDGF-BB. Here, the incubation mix contained 20 pM aptamers A1c and A2c in a 10 uL volume with 1 µL of the sample. The 40 µL ligation and detection mix was added and left at room temperature for 5 min, before the PCR reaction was started by heating the sample and thereby simultaneously stopping the ligation reaction. The ligation/detection mix contained T4 DNA ligase, ligation template (10+10) 40 nM, ATP, TaqGold DNA polymerase, dNTPs, PCR primers, and TaqMan probe.

A five fold dilution of the unbound proximity-probes is accomplished by the volume increase when the ligation/detection mix is added. This procedure also minimises the risk of contamination since the vessel is never opened for a second addition, and the sensitivity of the analysis increases through the dilution effect. 1×10E-19 moles of PDGF-BB was detected in the assay shown in FIG. 12. This is roughly a 500-fold increase in sensitivity over the reported sensitivity of commercial ELISAs for PDGF-BB.

EXAMPLE 2

Universal Proximity-probes

When detecting an analyte the proximity-probes must not always bind to the analyte itself, but can instead bind via a first affinity reagent. In the case of an analyte with two binding sites, the first affinity reagents bind the analyte and the proximity-probes bind to these primary reagents (FIG. 13). This strategy has advantages when designing universal proximity-probes here exemplified with antibodies as target-binding moieties.

The laborious conjugation of nucleic acid sequences to various antibodies or other binding moieties can be overcome by making universal proximity-probes. These would comprise a secondary pair of binding moieties, each one capable of binding once to the Fe region (constant region) of a primary binding antibody pair. The Fe region is constant for many different antibodies of various specificities. So, the nucleic acids are conjugated to these secondary binding moieties, and used universally for the detection of many different analytes. The primary antibody pair is incubated with the analyte and the secondary reactive binding reagents are added and allowed to preferentially react when in a high local concentration (FIG. 13).

EXAMPLE 3

Competitive Proximity-probing for Analytes with Only One Binding Site

It is not always the case that two binding moieties are available for an analyte. This can be overcome by using a competitive assay. Herein, a putrified amount of the analyte itself is conjugated to a nucleic acid and the one existing binding moiety is conjugated with the other reactive nucleic acid. When these two conjugates are permitted to react in a sample mixture containing an unknown amount of the analyte, the non-conjugated analyte of unknown amount in the sample will compete for binding to the binding moiety of the proximity-probe thereby decreasing the probability of the conjugated nucleic acids reacting. The signal from the reaction is in this case inversely proportional to the analyte concentration.

EXAMPLE 4

Multiplex Protein Detection Assay

Several analytes may be simultaneously detected by using several proximity-probe pairs, each specific for their distinct analyte. Those proximity-probe pairs have unique nucleic acid sequences in order to distinguish them from other pairs.

In one embodiment, the oligonucleotides all have the same PCR primer sites and the same ligation junction but unique identifier sequences. If different PCR primer sites and different ligation junctions are used, the risk of generating false PCR products due to cross reactivity will greatly increase which should be avoided. During the PCR the different amplicons representing the existence of different proteins are simultaneously amplified. These different PCR products may be detected by any of several methods, such as DNA microarrays, mass spectrometry, gel electrophoresis (different lengths of products), or other. A true positive ligation must contain both sequence identification tags form correct pairs of oligonucleotides in order to score as a true positive, FIG. 14. It is possible to use a DNA micro array for sorting unique amplification products corresponding to the presence of a certain protein.

EXAMPLE 5a

Screening Ligand Candidates in a Large Pool

Ligands to for example cell surface receptors can be found by screening cDNA expression clones for affinity towards said receptor. Such screening is usually carried out in various of solid phase formats where the known receptor is immobilised.

Proximity-probing provides an alternative means to screen large sets of ligand candidates without the need for a solid phase. One needs an antibody capable of binding to the known receptor in such a way that it blocks binding by the unknown receptor ligand. To the receptor an oligonucleotide is conjugated, that is capable of ligating to a second oligonucleotide conjugated to the antibody. To a set of sample mixtures, the receptor and antibody is added to interact with a potential receptor ligand. The ligation mix is added to the sample, and if a receptor ligand exists in the sample, ligation of the oligonucleotides will be inefficient due to the lack of nearness between them since receptor-antibody complexes fail to form in the prescene of the receptor ligand. A sample containing a potential ligand will therefore give a smaller signal. This method is not limited to receptors and their ligands, but could be used for all types of biomolecular interactions of interest.

EXAMPLE 5b

Screening Drug Candidates from Large Libraries

In a fashion similar to the one described for the unknown ligand screening method one can also screen for drug candidates. For example a receptor and its ligand are both conjugated with oligonucleotides. In a mixture containing a competitive drug candidate the ligation between the oligonucleotides will be inhibited since receptor ligand complexes fail to form large drug candidate libraries can thus be screened with minimal material use of receptor and its ligand.

EXAMPLE 6

Detection of Infectious Agents

By using probes with specificity for a surface molecule of an infectious agent such as a virus or an antibody, proximity probing could be used detect such agents at very low amounts. The two probes may be designed to bind to the same target if these are abundant on the surface and clustered near each other. The two probes may also bind to two different targets on the agent but also with the need to be near each other.

EXAMPLE 7

Target Analyte with More than Two Binding Sites

By using more than two proximity-probes per analyte a more sensitive detection can be accomplished. This assays is designed to require more than one ligation event to generate a signal. When three binding moieties can simultaneously bind the analyte, three different proximity-probes are made, each with different conjugated nucleic acid sequences. One with a 3' extension (A), one with a 5' extension (B), and one having both 3' and 5' extensions (C). The 3' end of A ligates to the 5' end of C and the 3' end of C ligates to the 5' end of B. In the case of PCR detection, the primers placed on A and B resulting in a PCR product spanning over the entire C probe. The C probe is preferentially constructed using a ssDNA aptamer binding moiety to facilitate the polymerisation over the nucleic acid conjugated to the C probe.

This strategy will decrease the background ligation due to the requirement of two ligation events for a false positive signal compared to one event as seen in the system with two ligatable proximity-probes. During assay optimisation, with decreasing proximity-probe concentration the likelyhood of background ligation decreases as the third root of the concentration compared to the squared root with the two-probe system.

EXAMPLE 8

Using a Dimerising Affinity Moieity

If only one binding moiety can be constructed into a proximity-probe a multimeric affinity reagent can create proximity by dimerising the analytes, enabling their detection. This can be exemplified by an aptamer based binding moiety constructed into a proximity-probe and an antibody which dimerises the analyte.

Many selex derived aptamers bind to only one site on the protein target. Since proximity probing requires the binding of at least two probes to each target in order to enable detection, these monovalent targets will be more difficult to detect. By adding to the incubation mixture a bivalent antibody (or other affinity reagent) capable of simultaneously binding two targets this may be overcome. The antibody must bind at a site separate from the selex aptamer so a complex of five molecules may form consisting of the antibody, two target proteins, and the two ligatable selex aptamer based proximity-probes.

In the presence of target, ligation of the aptamers is promoted by their proximity provided by the dimerising antibody. This system may alternatively be used to detect and quantify the antibody itself, by using constant amounts of the target and selex aptamer.

EXAMPLE 9

Screening for Ligand-receptor Interaction Antagonists

When searching for antagonists of a ligand-receptor interaction for pharmaceutical use a sensitive, specific and rapid testing system is beneficial in order to screen vast libraries of candidate compounds. This is sometimes referred to as high throughput screening.

The following is an example that shows how the PDLA detection system can be redesigned to test whether or not a compound binds a certain receptor. This screening principle is here exemplified by PDGF-BB and its receptor interaction. By adding a surplus of soluble receptor to an incubation mix of PDGF-BB and proximity-probes, the binding of the probes to pdgf is blocked by the receptor and no signal is generated. However, if a molecule which binds to the receptor in a competitive fashion is added to the incubation mix the PDGF is "liberated" and accessible to the proximity probes generating a signal.

In order to test this principle PDGF-AA was used to mimic the action of an antagonist since it is capable of binding the pdgf-alfa receptor but not the aptamers, 6,4 pM PDGF-BB was incubated with 5 pM of aptamer based proximity-probes and 2.5 nM of soluble PDGF-alpha receptor (in surplus). Upon addition of 100 nM PDGF-AA, which binds the receptor but not the aptamers, a 3-fold increase in signal was generated from the "liberated" PDGF-BB now accessible to the proximity-probes.

REFERENCES

1) Hart H E, Greenwald E B, Scintillation proximity assay (SPA)—a new method of immunoassay. Direct and inhibition mode detection with human albumin and rabbit antihuman albumin., Mol Immunol 1979 Apr.;16(4):265-7
2) Szollosi J, Damjanovich S, Matyus L, Application of fluorescence resonance energy transfer in the clinical laboratory: routine and research.Cytometry 1998 Aug. 15;34(4):159-79
3) Ueda H, Kubota K, Wang Y, Tsumoto K, Mohoney W, Kumagai I, Nagimune T, Homogeneous noncompetitive immunoassay based on the energy transfer between fluorolabeled antibody variable domains (open sandwich fluoroimmunoasssay)., Biotechniques 1999 Oct.;27(4):738-42
4) Koo E H, Lansbury P T, Jr, Kelly J W, Amyloid diseases: abnormal protein aggregation in neurodegeneration., Proc Natl Acad Sci USA 1999 Aug. 31;96(18):9989-90
5) Prusiner S B, McKinley M P, Bowman K A, Bolton D C, Bendheim P E, Groth D F, Glenner G G, Scrapie prions aggregate to form amyloid-like birefringent rods., Cell 1983 Dec.;35(2 Pt 1):349-58
6) Nadeau J G, Pitner J B, Linn C P, Schram J L, Dean C H, Nycz C M, Real-Time, Sequence-Specific Detection of Nucleic Acids during Strand Displacement Amplification.Anal Biochem 1999 Dec. 15;276(2):177-187
7) van Deursen P B, Gunther A W, van Riel C C, van der Eijnden M M, Vos H L, van Gemen B, van Strijp D A, Tackent N M, Bertina R M, A novel quantitative multiplex NASBA method: application to measuring tissue factor and CD14 mRNA levels in human monocytes.Nucleic Acids Res 1999 Sep. 1;27(17):e15
8) White S R, et al., Signal amplification system for DNA hybridization assays based on in vitro expression of a DNA label encoding apoaequorin., Nucleic Acids Res. 1999 Oct 1;27(19):e25.
9) Kwiatkowski R W, Lyamichev V, de Arruda M, Neri B, Clinical, Genetic, and Pharmacogenetic Applications of the Invader Assay., Mol Diagn 1999 Dec.;4(4):353-364
10) Gibson, U. E., heid, C. A., Williams, P. M. Genome Res., 6, 995-1001
11) Tyagi, S. Kramer, F. R. Molecular beacons: probes that fluoresce upon hybridization, Nat Biotechnol(1996), 14, 3, 303-8
12) Steuerwald N, Cohen J, Herrera R J, Brenner C A, Analysis of gene expression in simple oocytes and embryos by real-time rapid cycle fluorescence monitored RT-PCR.Mol Hum Reprod 1999 Nov.;5(11):1034-9
13) Gentalen E, Chec M, A novel method for determining linkage between DNA sequences: hybridization to paired probe arrays., Nucleic Acids Res 1999 Mar. 15;27(6):1485-91
14) Baner J, Nilsson M, Mendel-Hartvig M, Landegren U, Signal amplification of padlock probes by rolling circle replication., Nucleic Acids Res 1998 Nov. 15;26(22):5073-8
15) Nilsson M, Malmgren H, Samiotaki M, Kwiatkowski M, Chowdhary B P, Landegren U, Padlock probes: circularizing oligonucleotides for localized DNA detection., Science 1994 Sep 30;265(5181):2085-8
16) Gold, L. Polisky, B. Uhlenbeck, O. Yarus, M., Diversity of oligonucleotide functions. Annu Rev Biochem, 1995, 64, 763-97
17) Green, L. S. Jellinek, D. Jenison, R. Ostman, A. Heldin, C. H. Janjic, N., Inhibitory DNA ligands to platelet-derived growth factor B-chain, Biochemistry, 1996, 35, 45, 14413-24

The invention claimed is:

1. A method for detecting the presence of one or more analytes in solution, comprising:
   a) binding two or more proximity probes to a respective binding site on said one or more analytes not immobilized on a solid support,
   wherein each proximity probe comprises a binding moiety with affinity for said one or more analytes and nucleic acids acting as a reactive functionality coupled to the binding moiety;
   b) allowing the binding moiety to bind to the one or more analytes other than by Watson-Crick base pairing and allowing the nucleic acids of the proximity probes to interact with each other if the proximity probes are in close proximity to each other; and
   c) detecting the degree of interaction between the nucleic acids, thereby detecting the presence of one or more analytes in solution.

2. A method according to claim 1, further comprising amplification of the interacted nucleic acids and quantification of the amplification product.

3. A method according to claim 1, wherein the binding moiety of the proximity probes is selected from the group consisting of proteins, peptides, carbohydrates, nucleic acids and combinations thereof.

4. A method according to claim 1, wherein the one or more analytes are selected from the group consisting of proteins, protein aggregates, prions and nucleic acids.

5. A method according to claim 1, wherein the binding sites for the binding moieties of the proximity probes are on one and the same analyte, or on two close analytes.

6. A method according to claim 1, wherein the binding moieties are antibodies and said antibodies each bind to the one or more analytes via a further antibody having binding specificity for the one or more analytes analyte(s), and wherein the binding moieties are directed against the Fc portion of the further antibody.

7. A method according to claim 1, wherein the interaction of said nucleic acids coupled to the binding moieties is through hybridisation to a common splint template and ligation of the nucleic acid ends.

8. A method according to claim 1 for screening for ligand-receptor interaction antagonists in a high throughput screening procedure, wherein a drug candidate molecule is screened for ability to disrupt proximity between the proximity probes.

9. A method according to claim 1, wherein the first proximity probe comprises a purified analyte coupled to an oligonucleotide and the second proximity probe comprises a binding moiety specific for the analyte and coupled to an oligonucleotide which interacts with the oligonucleotide of the first proximity probe if the first and second proximity probes are in close proximity.

10. A method according to claim 1, further comprising screening a drug candidate molecule, which is a biomolecule derived from a library of potential ligands, for the ability to disrupt proximity between the proximity probes by binding to one of the binding sites involved in the formation of the proximity between the proximity probes.

11. A method according to claim 1, comprising using said method for the detection of infectious agents.

12. A method according to claim 11, wherein the infectious agents are detected in food for humans and animals.

13. The method according to claim 1, further comprising quantifying the interaction of the analytes in solution.

14. A method according to claim 13, further comprising amplification of the interacted nucleic acids and quantification of the amplification product.

15. A method according to claim 9, wherein the presence of an analyte in a sample is detected as a decrease in signal.

16. A method according to claim 1, wherein said two or more proximity probes comprise a first said proximity probe with a 3' free nucleic acid (A), a second said proximity probe with a 5' free nucleic acid (B), and a third said proximity probe with both 3' and 5' free nucleic acids (C), and wherein the 3' end of A interacts with the 5' end of C and the 3' end of C interacts with the 5' end of B.

17. A method according to claim 3, wherein the proteins are selected from the group consisting of monoclonal antibodies, polyclonal antibodies, lectins, soluble cell surface receptors, combinatorially derived proteins from phage display, and combinatorially derived proteins from ribosome display.

18. The method of claim 3, wherein the nucleic acids are aptamers.

19. The method of claim 1, wherein the one or more analytes are selected from the group consisting of proteins, protein aggregates, and prions.

20. The method of claim 1, wherein the one or more analytes are not nucleic acids.

21. A method for detecting one or more analytes in solution, comprising:
 a) binding two or more proximity probes to a respective binding site on said one or more analytes not immobilized on a solid support, wherein the proximity probes comprise a binding moiety with affinity for said one or more analytes and nucleic acids acting as a reactive functionality coupled thereto;
 b) allowing the binding moiety to bind to the one or more analytes other than by Watson-Crick base pairing and allowing the nucleic acids to interact with each other if they are in close proximity to each other; and
 c) detecting the degree of interaction between the nucleic acids.

* * * * *

SEQUENCE LISTING

```
<160> NUMBER OF SEQ ID NOS: 4

<210> SEQ ID NO 1
<211> LENGTH: 86
<212> TYPE: DNA
<213> ORGANISM: Artificial Sequence
<220> FEATURE:
<223> OTHER INFORMATION: primer

<400> SEQUENCE: 1
tactcagggc actgcaagca attgtggtcc caatgggctg agtatgtggt ctatgtcgtc      60
gttcgctagt agttcctggg ctgcac                                           86

<210> SEQ ID NO 2
<211> LENGTH: 80
<212> TYPE: DNA
<213> ORGANISM: Artificial Sequence
<220> FEATURE:
<223> OTHER INFORMATION: primer

<400> SEQUENCE: 2
tcgaggcgta gaattccccc gatgcgcgct gttcttactc agggcactgc aagcaattgt      60
ggtcccaatg ggctgagtat                                                  80
```

```
<210> SEQ ID NO 3
<211> LENGTH: 26
<212> TYPE: DNA
<213> ORGANISM: Artificial Sequence
<220> FEATURE:
<223> OTHER INFORMATION: unknown

<400> SEQUENCE: 3
gggggaattc tacgcctcga gtgcag                                        26

<210> SEQ ID NO 4
<211> LENGTH: 26
<212> TYPE: DNA
<213> ORGANISM: Artificial Sequence
<220> FEATURE:
<223> OTHER INFORMATION: unknown

<400> SEQUENCE: 4
aaatacgcct cgagtgcagc ccattt                                        26
```